United States Patent
Hugentobler et al.

(10) Patent No.: US 9,162,969 B2
(45) Date of Patent: Oct. 20, 2015

(54) NITROOXYESTERS, THEIR PREPARATION AND USE

(75) Inventors: Max Hugentobler, Arlesheim (CH); Steffen Ruf, Rheinfelden (CH); Bettina Wuestenberg, Möhlin (CH)

(73) Assignee: DSM IP ASSETS B.V., Heerlen (NL)

( * ) Notice: Subject to any disclaimer, the term of this patent is extended or adjusted under 35 U.S.C. 154(b) by 640 days.

(21) Appl. No.: 13/393,656

(22) PCT Filed: Sep. 14, 2010

(86) PCT No.: PCT/EP2010/063462
§ 371 (c)(1),
(2), (4) Date: May 8, 2012

(87) PCT Pub. No.: WO2011/032936
PCT Pub. Date: Mar. 24, 2011

(65) Prior Publication Data
US 2012/0210634 A1    Aug. 23, 2012

Related U.S. Application Data

(60) Provisional application No. 61/242,430, filed on Sep. 15, 2009.

(51) Int. Cl.
*C10L 1/23* (2006.01)
*C07C 203/00* (2006.01)
(Continued)

(52) U.S. Cl.
CPC ............... *C07C 203/04* (2013.01); *C10L 1/238* (2013.01)

(58) Field of Classification Search
CPC .. C07C 203/02; C07C 203/04; C07C 203/08; C07C 203/10; C10L 1/23; C10L 1/231; C10L 2230/22

USPC ............. 558/480–487; 44/323, 324, 326
See application file for complete search history.

(56) References Cited

U.S. PATENT DOCUMENTS 4,536,190 A * 8/1985 Seemuth .................. 44/324
4,549,883 A * 10/1985 Purcell et al. ............ 44/324
(Continued)

FOREIGN PATENT DOCUMENTS

| WO | WO 00/61537 | 10/2000 |
|---|---|---|
| WO | WO 2005/003263 | 1/2005 |
| WO | WO 2005/068421 | 7/2005 |

OTHER PUBLICATIONS

International Search Report for PCT/EP2010/063462 mailed Jan. 28, 2011.
(Continued)

*Primary Examiner* — Ellen McAvoy
(74) *Attorney, Agent, or Firm* — Nixon & Vanderhye P.C.

(57) ABSTRACT

The present invention relates to the novel compounds of the formula (I), as well as to their manufacture and use and compositions comprising them. The invention also relates to a change in oxidation reactions of hydrocarbons admixed to these compounds. Furthermore the invention relates to (bio) diesel fuel comprising such compounds.

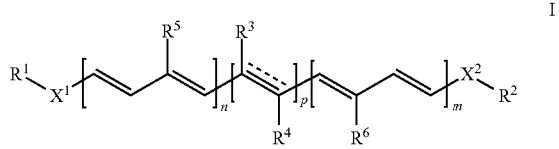

32 Claims, 7 Drawing Sheets

(51) Int. Cl.
*C07C 203/04* (2006.01)
*C10L 1/238* (2006.01)

(56) References Cited

U.S. PATENT DOCUMENTS

| | | | | |
|---|---|---|---|---|
| 4,561,862 | A | | 12/1985 | Dory |
| 5,454,842 | A | * | 10/1995 | Poirier et al. .................. 44/324 |
| 5,482,518 | A | * | 1/1996 | Poirier .......................... 44/312 |
| 5,669,938 | A | * | 9/1997 | Schwab ......................... 44/301 |
| 5,782,937 | A | * | 7/1998 | Colucci et al. ................. 44/324 |
| 6,638,324 | B2 | | 10/2003 | Jordan |
| 7,169,809 | B2 | * | 1/2007 | Berthelette et al. ........... 514/509 |
| 7,615,085 | B2 | * | 11/2009 | Schwab et al. ................. 44/387 |
| 7,723,529 | B2 | * | 5/2010 | Almirante et al. ............ 548/250 |
| 8,709,110 | B2 | * | 4/2014 | Hugentobler et al. ......... 44/388 |
| 2005/0192346 | A1 | * | 9/2005 | Shi et al. ....................... 514/509 |
| 2009/0320354 | A1 | * | 12/2009 | Kormann et al. ............... 44/325 |
| 2010/0293841 | A1 | * | 11/2010 | Zuckerman .................... 44/325 |
| 2010/0325944 | A1 | * | 12/2010 | Yang et al. ..................... 44/322 |
| 2012/0066964 | A1 | * | 3/2012 | Harrell et al. ................... 44/322 |

OTHER PUBLICATIONS

R. Annunziata et al., "Stereoselective Intramolecular Nitrone Cycloadditions Promoted by an Allylic Stereocenter", Journal of Organic Chemistry, 55(6), 1990, XP002610296, 8 pages.

M. Melnick et al., "Intramolecular Cycloaddition Reactions of N-acyl Imines. A Stereoselective Approach to the N-terminal Amino Acid Component of Nikkomycin B", Journal of Organic Chemistry 53(4), 1988,XP002610297, 5 pages.

B. Snider, et al., "Total Synthesis of (.+-.)—Deoxypenostatin A. Approaches to the Syntheses of Penostatins A and B", Journal of Organic Chemistry, 65(25), 2000, XP002610298, 9 pages.

D. Tschaen et al., "Stereochemical Studies of Thermal Intermolecular and Intramolecular N-sulfonylimine ene Reactions", Journal of Organic Chemistry, 49(26), 1984, XP002610299, 7 pages.

B. Snider et al., "Total Synthesis of (.+-.)—Deoxypenostatin A", Journal of Organic Chemistry, 64(4), 1999, XP002610300, 2 pages.

* cited by examiner

NITROOXYESTERS, THEIR PREPARATION AND USE

This application is the U.S. national phase of International Application No. PCT/EP2010/063462 filed 14 Sep. 2010 which designated the U.S. and claims priority to U.S. Provisional Application No. 61/242,430 filed 15 Sep. 2009, the entire contents of each of which are hereby incorporated by reference.

FIELD OF THE INVENTION

The present invention relates to compounds of the formula I (nitrooxyesters), their manufacture as well as to compositions comprising them. The invention also relates to a change in oxidation reactions of hydrocarbons admixed to these compounds/compositions.

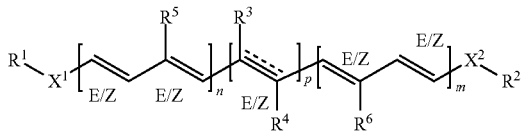

The present invention is further directed to nitrooxyesters of carotenoids and nitrooxyesters of xanthophylls, wherein the carotenoids or xanthophylls can either be synthesized or isolated from natural sources and contain at least one hydroxy group which has reacted with $X(CO)L[ONO_2]_x$ as defined below.

The present invention relates to a composition comprising
a) a compound selected from the group consisting of compounds of the formula I (nitrooxyester), nitrooxyesters of carotenoids, nitrooxyesters of xanthophylls and any mixtures thereof; and
b) a substance selected from the group of alkyl nitrates, nitrooxy esters of alkoxy substituted aliphatic alcohols, organic peroxides and mixtures thereof.

The invention also relates to a change in oxidation reactions of hydrocarbons, especially of fuels, admixed to these compositions.

Moreover, the present invention relates to a composition comprising
a) a compound selected from the group consisting of compounds of the formula I (nitrooxyester), nitrooxyesters of carotenoids, nitrooxyesters of xanthophylls and any mixtures thereof; and
c) a hydrocarbon, especially a fuel.

Furthermore, the present invention relates to a composition comprising
a) a compound selected from the group consisting of compounds of the formula I (nitrooxyester), nitrooxyesters of carotenoids, nitrooxyesters of xanthophylls and any mixtures thereof; and
b) a compound selected from the group consisting of alkyl nitrates, nitrooxy esters of alkoxy substituted aliphatic alcohols, organic peroxides and mixtures thereof; and
d) a stabilizing compound; and
e) optionally a solvent. (A solvent is present if needed to further increase the solubility in the fuel or the hydrocarbon in general.)

Such a composition comprising compounds a), b) and d) or a), b), d) and e) may be used as fuel additive.

BACKGROUND OF THE INVENTION

Fuel efficiency can be improved by adding additives to hydrocarbons. Several patents have aimed to enhance the efficiency of fuel combustion with additives that contain carotenoids, e.g. U.S. Pat. No. 6,638,324.

There still is a need for compositions that improve the oxidation of hydrocarbons, especially the oxidation of fuels.

EMBODIMENTS OF THE INVENTION

The invention relates to
compounds of the formula I as defined below, as well as to synthetic carotenoids/xanthophylls that have reacted with $X(CO)L[ONO_2]_x$ as defined below,
to carotenoids/xanthophylls from natural sources that have reacted with $X(CO)L[ONO_2]_x$ as defined below and to compositions containing either of them or any mixture of them.

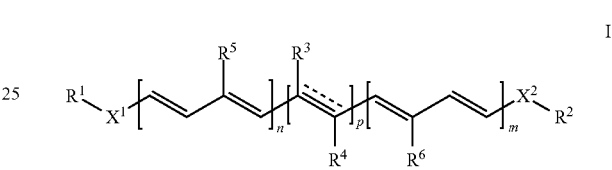

In formula I n, m and p are independently from each other integers from 0 to 50, with the proviso that at least one of n, m and p is not 0 and with the further proviso that n+p+m is at most 50;

$X^1$ and $X^2$ are independently from each other an oxo group or a hydrocarbon moiety, which may contain (a) C=C double bond(s) and/or (an) oxy group(s) and/or (an) oxygen atom(s),
$R^1$ and $R^2$ are independently from each other hydrogen, hydroxy, alkoxy or $O(CO)L[ONO_2]_x$ with L being a straight alkylene having 2 to 25 carbon atoms, a branched or cyclic alkylene having 3 to 25 carbon atoms or an arylene having 6 to 16 carbon atoms or an alkylarylene having 7 to 16 carbon atoms such as e.g. tolyl, (o-, m-, p-) xylyl, and mesityl, and with x being an integer ≥1 depending on the chain length;
$R^3$ and $R^4$ are independently from each other hydrogen or in case of a triple bond both do not exist;
$R^5$ and $R^6$ are independently from each other hydrogen or $C_{1-6}$ alkyl (straight, branched or cyclic; preferably linear or branched, more preferably linear/straight, most preferably methyl); and
with the proviso that the compound of formula I itself contains at least one $O(CO)L[ONO_2]_x$ group as defined above.

The double bonds in formula I may be trans or cis. Thus formula I covers the all-trans form well as any cis-isomers thereof (mono-cis, di-cis, etc.).

In case $X^1$ or $X^2$ is an oxo group (CO) and $R^1$ or $R^2$ is hydrogen (H), $X^1R^1$ or $X^2R^2$, respectively, is CHO—an aldehyde.

In case $X^1$ or $X^2$ is an oxo group (CO) and $R^1$ or $R^2$ is hydroxy (OH), $X^1R^1$ or $X^2R^2$, respectively, is COOH—a carboxylic acid.

In case $X^1$ or $X^2$ is an oxo group (CO) and $R^1$ or $R^2$ is alkoxy (OR), $X^1R^1$ or $X^2R^2$, respectively, is COOR—an ester.

If there is a triple bond between the C-atoms bearing $R^3$ and $R^4$ in the formula I drawn above, $R^3$ and $R^4$ do not exist, i.e. with a triple bond at this position formula I looks like the following formula A:

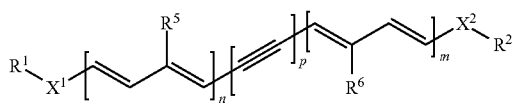

A

Within the present invention the notation n, m and p also comprises the embodiment wherein the substituents $R^3$, $R^4$, $R^5$ and $R^6$, respectively, are different within each n, m and p, meaning e.g. if n=2 that there is a C(H)=C(H)CR$^5$=C(H)—C(H)=C(H)CR$^{5'}$=C(H) unit, wherein $R^5$ and $R^{5'}$ may be equal or different to each other. The same applies for p and m accordingly meaning that each p unit may or may not contain a double bond ($R^3$=$R^4$=H) or a triple bond independent from the other p unit. If there is indeed a triple bond in formula I, p is preferably 1.

A compound, where n=2; and m=0 and p=0 may for example look like the following formula B:

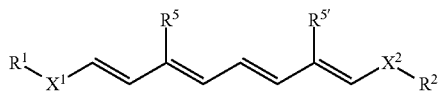

B

The present invention is further directed to a process for the manufacture of compounds of formula I

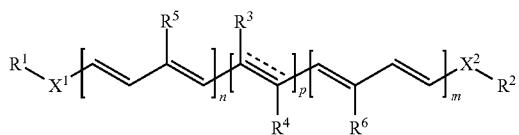

I comprising the step of reacting a compound of formula V

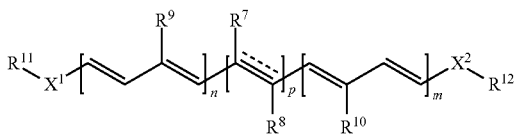

V with an acid of the formula HO(CO)L[ONO$_2$]$_x$ or an acid anhydride of the formula [O$_2$NO]$_x$L(CO)O(CO)L[ONO$_2$]$_x$ or an acid halide of the formula X(CO)L[ONO$_2$]$_x$ with X being Br or Cl and L being a straight alkylene having 2 to 25 carbon atoms, a branched or cyclic alkylene having 3 to 25 carbon atoms or an arylene having 6 to 16 carbon atoms or an alkylarylene having 7 to 16 carbon atoms such as e.g. tolyl, (o-, m-, p-)xylyl, and mesityl, and with x being an integer ≥1 depending on the chain length (preferably x=1 or 2, more preferably x=1);
wherein n, m and p, $X^1$, $X^2$ and $R^1$-$R^6$ are as defined above;
$R^{11}$ and $R^{12}$ are independently from each other hydrogen, hydroxy or alkoxy;
$R^7$ and $R^8$ are independently from each other hydrogen or in case of a triple bond both do not exist;
$R^9$ and $R^{10}$ are independently from each other hydrogen or $C_{1-6}$ alkyl (straight $C_{1-6}$ alkyl, branched or cyclic $C_{3-6}$ alkyl; preferably linear or branched, more preferably linear/straight); and with the proviso that the compound of formula I itself contains at least one hydroxy group.

The esterification of the compounds of formula V with the acid HO(CO)L[ONO$_2$]$_x$ or its halide or its anhydride to the compounds of formula I may be carried out according to any standard esterification method know to the person skilled in the art.

Compounds of formula V as defined above may e.g. be reacted with an acid HO(CO)L[ONO$_2$]$_x$ in the presence of a dehydrating agent [e.g. N,N'-dicyclo-hexylcarbodiimide (DCC) and an aminopyridine (like dimethylaminopyridine (DMAP)] in an organic solvent such as CH$_2$Cl$_2$ to obtain compounds of formula I. This reaction may be carried out at a temperature in the range of from 0° C. to 150° C.

Alternatively compounds of formula V may be reacted with an acyl halide X(CO)L[ONO$_2$]$_x$ (preferably X=Cl or Br) in the presence of a base (e.g. aqueous alkali hydroxide or an amine such as pyridine) to compounds of formula I.

Furthermore, acid anhydrides [(O$_2$NO)$_x$L(CO)]$_2$O (or mixed acid anhydrides) can be reacted with compounds of formula V to compounds of formula I in the presence of an acid, a Lewis acid or a base as catalyst (e.g. pyridine, DMAP) in an organic solvent. This possibility is, however, not preferred.

The invention further relates to a composition comprising
a) a compound selected from the group consisting of compounds of the formula I (nitrooxyester), nitrooxyesters of carotenoids, nitrooxyesters of xanthophylls and any mixtures thereof; and
b) a substance selected from the group of alkyl nitrates, nitrooxy esters of alkoxy substituted aliphatic alcohols, organic peroxides and mixtures thereof.

The invention also relates to a method of oxidizing a hydrocarbon, comprising bringing the hydrocarbon in contact with the compounds/compositions of the invention, especially with the compound(s) a) and b), and oxidizing at least part of the hydrocarbon.

The invention further relates to a mixture of compounds/compositions of the invention with a diesel fuel.

Moreover, the present invention relates to a composition comprising
a) a compound selected from the group consisting of compounds of the formula I (nitrooxyester), nitrooxyesters of carotenoids, nitrooxyesters of xanthophylls and any mixtures thereof; and
c) a fuel.

The present invention is further directed to a composition comprising
a) a compound selected from the group consisting of compounds of the formula I (nitrooxyester), nitrooxyesters of carotenoids, nitrooxyesters of xanthophylls and any mixtures thereof; and
c) a hydrocarbon.

The composition of compound(s) a) and c) may further comprise a compound b) as defined above.

Furthermore, the present invention relates to a composition comprising
a) a compound selected from the group consisting of compounds of the formula I (nitrooxyester), nitrooxyesters of carotenoids, nitrooxyesters of xanthophylls and any mixtures thereof; and
b) a compound selected from the group of alkyl nitrates, nitrooxy esters of alkoxy substituted aliphatic alcohols, organic peroxides and mixtures thereof; and
d) a stabilizing compound as defined below; and
e) optionally a solvent. (A solvent is present if needed to further increase the solubility in the fuel.)

Surprisingly it was found that the nitrooxyesters according to the present invention and thus also compositions containing it showed better solubility in fuel additives than isomixtene. That means that the fuel additives can be prepared with less solvent.

DETAILED DESCRIPTION

Figure 1:
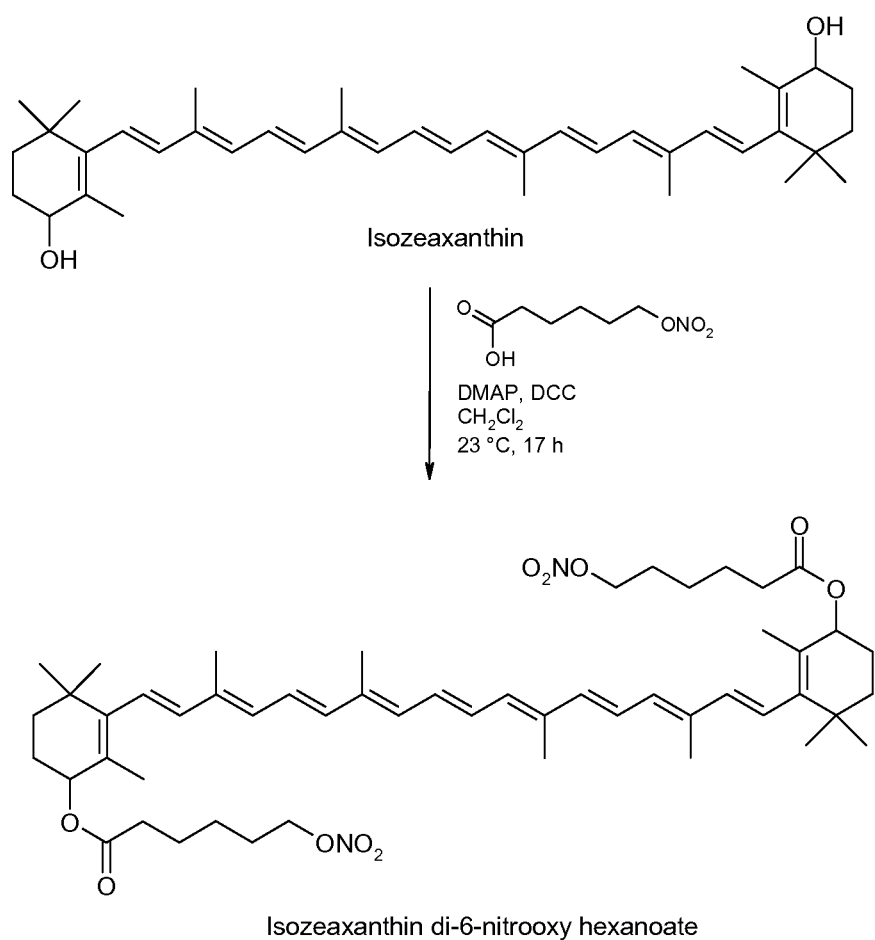
FIG. 1 depicts a reaction scheme to obtain isozeaxanthin di-6-nitrooxy hexanoate from isozeaxanthin.

The term "a substance"/"a compound" encompasses the situation that at least one substance/compound is present meaning one or more substance(s)/compound(s) may be present. This applies for all compounds a) to e).

The Compound a)

The expression "compound a)" also encompasses nitrooxyesters of carotenoids and nitrooxyesters of xanthophylls and any mixtures thereof, wherein the carotenoids or xanthophylls can either be synthesized or isolated from natural sources and contain at least one hydroxy group which has reacted with $X(CO)L[ONO_2]_x$ as defined above. The expression "compound a)" in the context of the present invention also encompasses mixtures of mono-nitrooxyesters, mixtures of di-nitrooxyesters and mixtures of mono- and dinitrooxyesters, as well as mixtures of carotenoids and/or xanthophylls with their mono- and/or di-nitrooxyesters. The same applies accordingly for "higher order nitrooxyesters" such as tri-nitroxyesters, quarter-nitrooxyesters etc.

Mixtures of nitrooxyesters of synthetic carotenoids/xanthophylls, as well as mixtures of nitrooxyesters of synthetic ones with nitrooxyesters of those isolated from natural sources, whereby the nitrooxyesters of carotenoids/xanthophylls may further contain other functional groups, i.e. may be substituted or not-substituted, are also encompassed by the expression "compounds a) of the present invention".

Natural sources encompass plants, fungi and microorganism.

The term "plants" encompasses any part of a plant such as e.g. fruits, leaves, roots and flowers. The isolation from natural sources may e.g. be achieved by extraction.

By the isolation from natural sources not only single carotenoids may be isolated that may further be reacted with $X(CO)L[ONO_2]_x$, but also mixtures of carotenoids, such as e.g. lutein and zeaxanthin.

Carotenoids that do not contain a hydroxy group may further be hydroxylated or submitted to any other reaction suitable to introduce a hydroxy group.

The term "carotenoids" in the context of the present invention encompasses a class of compounds built from 8 isoprene units in such a manner that the linking of the isoprene units is reversed in the middle of the molecule. As a result, the two methyl groups near the centre of the polyene chain are separated by 6 C-atoms and the other methyl groups by 5 C-atoms.

Preferably the carotenoids or xanthophylls contain up to 45 C atoms without the nitrooxy ester groups $O(CO)L[ONO_2]_x$,

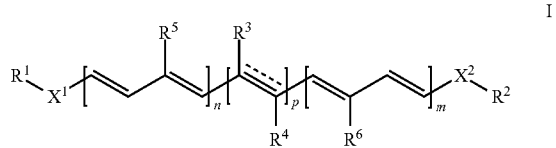

In the compositions of the present invention enantiomeric pure compounds of formula I may be used as well as any mixture of them including the racemate. This also applies for the nitrooxyesters of carotenoids and the nitrooxyesters of xanthophylls.

Besides all-E-stereoisomers of the compounds of formula I all other stereoisomers (mixed E/Z-isomers) may be used.

The compound a) may be stabilized with tocopherol and/or tocopherol acetate, preferably with less than 10% by weight (wt.-%) of tocopherol and/or tocopherol acetate based on the weight of compound a), more preferably between 0.1% and 5 wt. % of tocopherol and/or tocopherol acetate, most preferably between 0.5 and 3 wt. % of tocopherol and/or tocopherol acetate.

The compound a) may also be mixed with synthetic or natural β-carotene, especially with synthetic β-carotene. Such synthetic β-carotene consisting of cis and trans stereoisomers is e.g. commercially available under the product name "isomixtene" from DSM Nutritional Products Ltd (Kaiseraugst, Switzerland). Preferably such synthetic β-carotene contains from about 89 weight-% to about 98.6 weight-% all-trans β-carotene and about 1.4 weight-% to about 11 weight-% of a mixture of cis β-carotene isomers (especially the 13Z-β-carotene isomer).

Preferred Compounds of Formula I

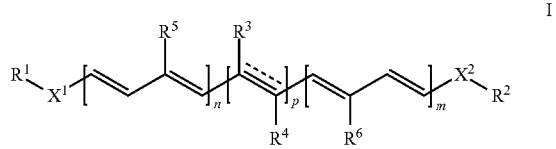

Preferably $X^1$ and $X^2$ are independently from each other an oxo group or a $C_{1-25}$ hydrocarbon moiety, more preferably a $C_{2-20}$ hydrocarbon moiety, even more preferably a $C_{8-14}$ hydrocarbon moiety. The hydrocarbon moiety may contain one or more C═C double bonds, one or more oxy groups and/or one or more oxygen atoms.

Preferably $R^1X^1$ and $R^2X^2$ are selected from the group consisting of the following groups:

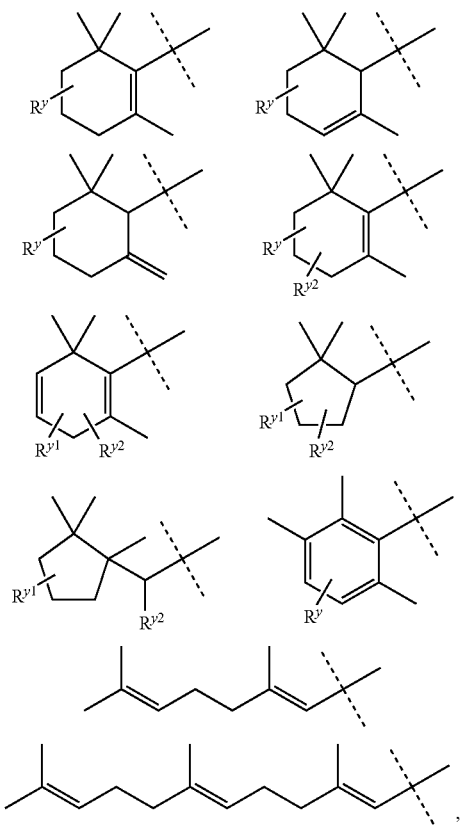

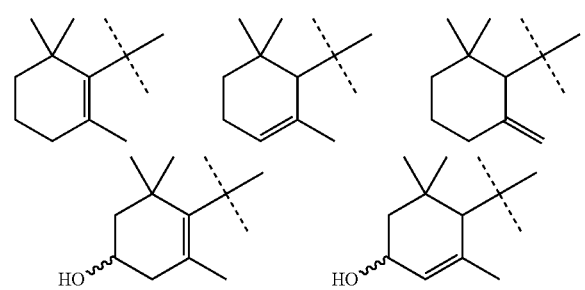

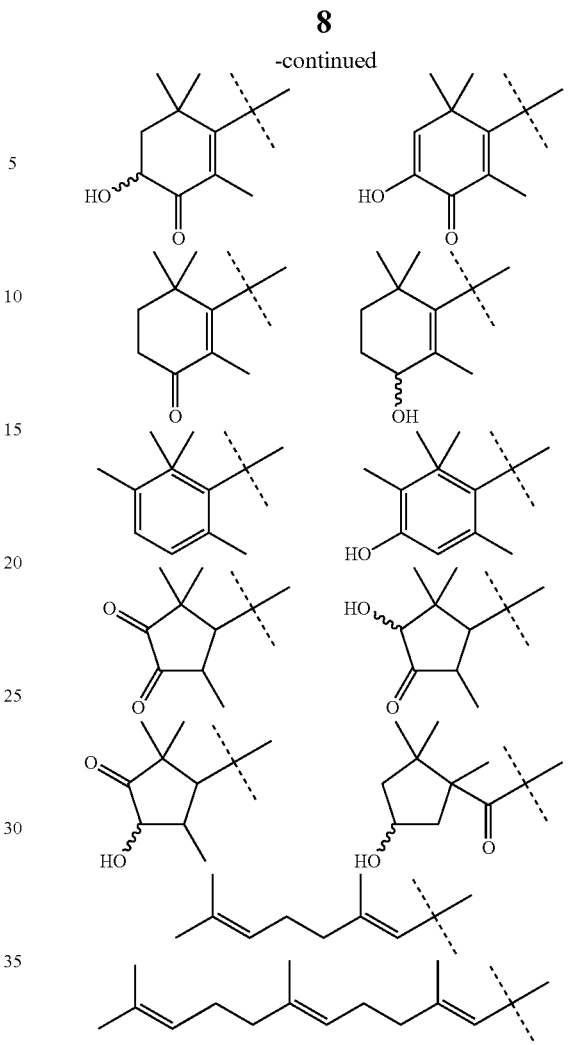

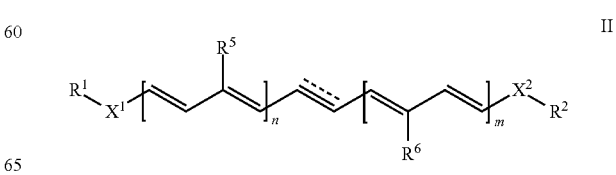

wherein $R^y$, $R^{y1}$ and $R^{y2}$ are independently from each other hydrogen, hydroxy, oxo (i.e. $R^{y(1/2)}$—C is O═C) or O(CO)L[ONO$_2$]$_x$ with L being a straight alkylene having 2 to 25 carbon atoms, a branched alkylene having 3 to 25 carbon atoms or a cyclic alkylene having 3 to 25 carbon atoms and with x being an integer from 1 to 3 (preferably x=1 or 2, more preferably x=1); with the proviso that at least one O(CO)L[ONO$_2$]$_x$ group is present in the compound of the formula I. This means that at least one of the groups shown above with $R^y$, $R^{y1}$ and/or $R^{y2}$ being O(CO)L[ONO$_2$]$_x$ is present in the molecule.

Preferably $R^1X^1$ and $R^2X^2$ are selected from the group consisting of the following groups:

with the proviso that at least one O(CO)L[ONO$_2$]$_x$ group is present in the compound of the formula I, which means that at least one hydroxy group has reacted with an acid, acid halide or acid anhydride to introduce such a group O(CO)L[ONO$_2$]$_x$ into the molecule.

Preferably $R^3$ and $R^4$ are both hydrogen or both do not exist (=triple bond), more preferably $R^3$ and $R^4$ are both hydrogen.

Preferably $R^5$ and $R^6$ are independently from each other hydrogen or methyl, more preferably they are both methyl.

Preferably n=m≥1 and p≠0, more preferably n=m=2 and p=1.

Preferred compounds of formula I wherein p=1 are those, wherein n=m=2 and $R^3=R^4$=H. These encompass carotenoids/xanthophylls substituted with O(CO)L[ONO$_2$]$_x$ as defined above.

Most Preferred Compounds a)

Preferred are compounds wherein p=1, i.e. compounds of formula II with $X^1$, $X^2$, $R^1$, $R^2$, $R^5$, $R^6$ and n and m as defined above.

The formula I as defined above encompasses more preferably compounds, wherein $R^3=R^4=H$, $R^5=R^6=CH_3$, p=1 and either $R^1$ or $R^2$ or both are $O(CO)LONO_2$. The compounds of the formula Ia ($R^1=O(CO)LONO_2$), as well as compounds of the formula Ib ($R^2=O(CO)LONO_2$) have one nitrooxy group each. Compounds of formula Ic ($R^1=R^2=O(CO)LONO_2$) have two nitrooxy groups.

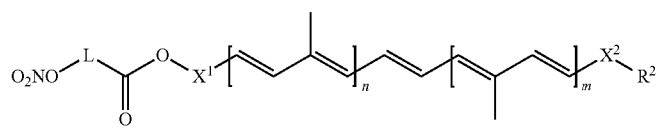

Ia

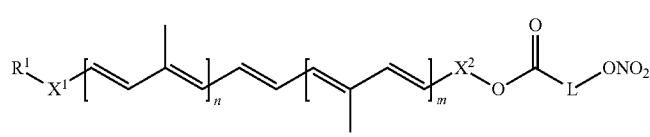

Ib

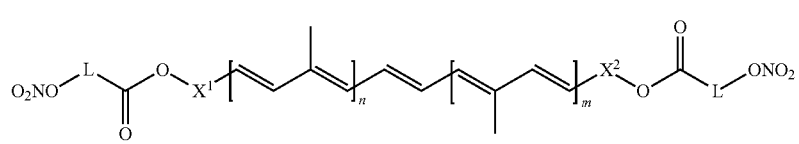

Ic

Even more preferred are compounds of formula I, wherein p=1 and n, m=2, i.e. compounds of the formula III

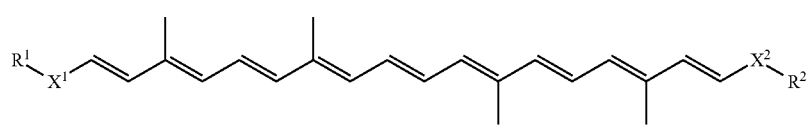

III with $X^1$ and $X^2$ and $R^1$ and $R^2$ as defined above.

Most preferred are compounds of formula I, wherein p=1; n, m=2 and $X^1$ and $X^2$ are each 2,6,6-trimethyl-1-cyclohexendiyl and $R^1$ and $R^2$ are each $O(CO)LONO_2$, i.e. compounds of formula IV wherein L is a straight alkylene having 2 to 25 carbon atoms, a branched alkylene having 3 to 25 carbon atoms or a cyclic alkylene having 3 to 25 carbon atoms or arylene having 6 to 16 carbon atoms or alkylarylene having 7 to 16 carbon atoms. The compound of formula IV is isozeaxanthin dinitrooxyester.

Figure 3:
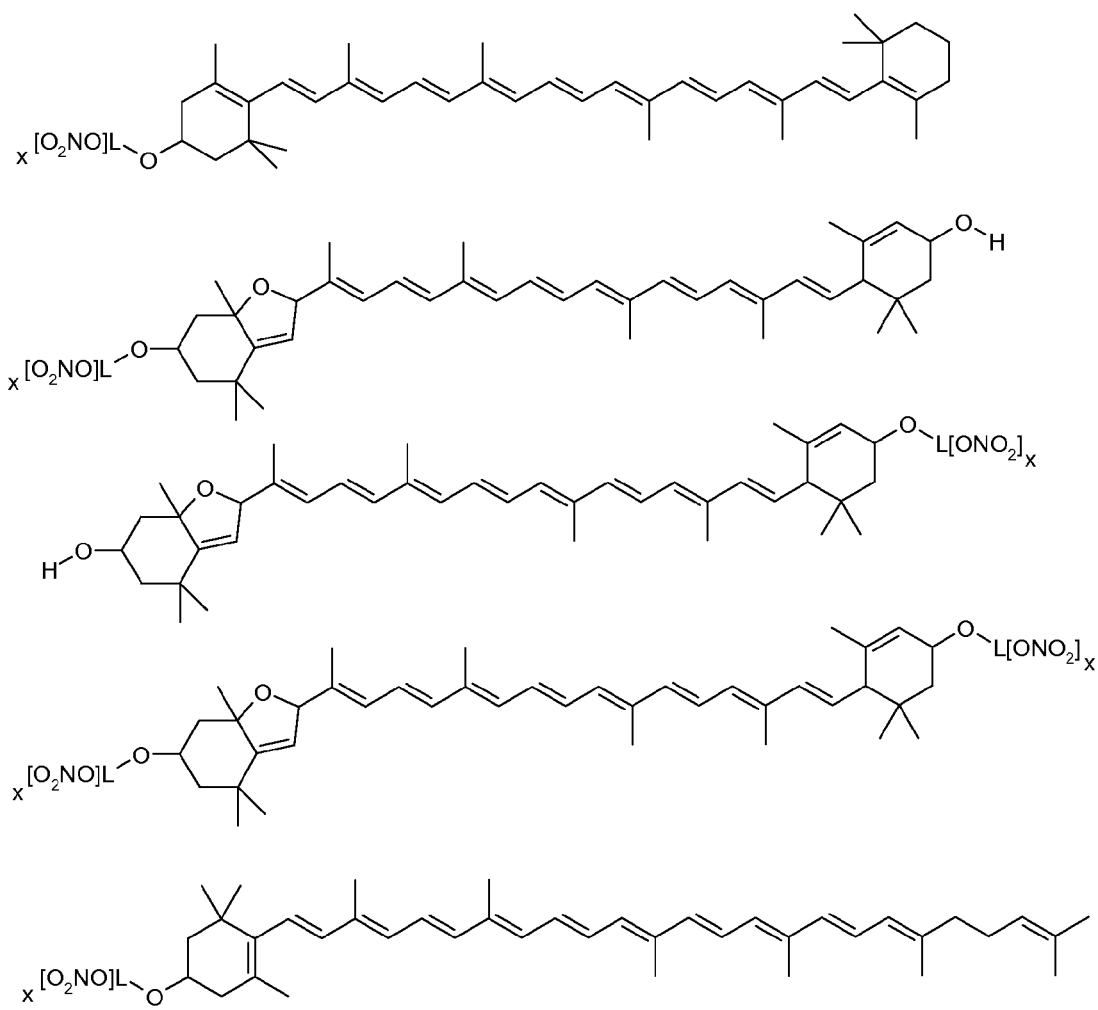
FIG. 3 are structural formulas depicting nitrooxyesters of xanthophylls such as cryptoxanthin nitrooxy alkanoate, flavoxanthin nitrooxy alkanoates, flavoxanthin dinitrooxy dialkanoate, and rubixanthin nitrooxy alkanoate.
Figure 4:
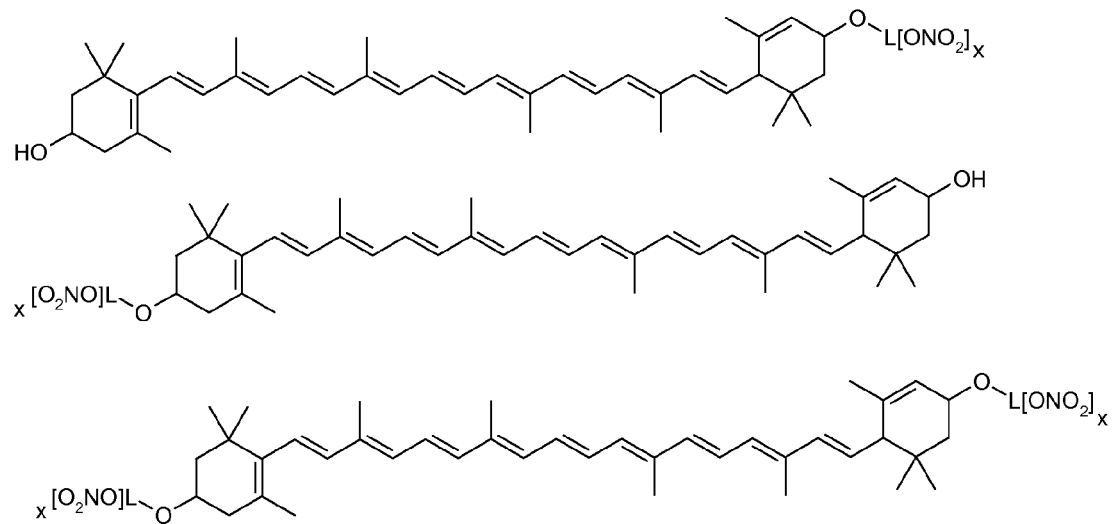
FIG. 4 are structural formulas depicting lutein nitrooxy alkanoates and lutein dinitrooxy alkanoates.
Figure 5:
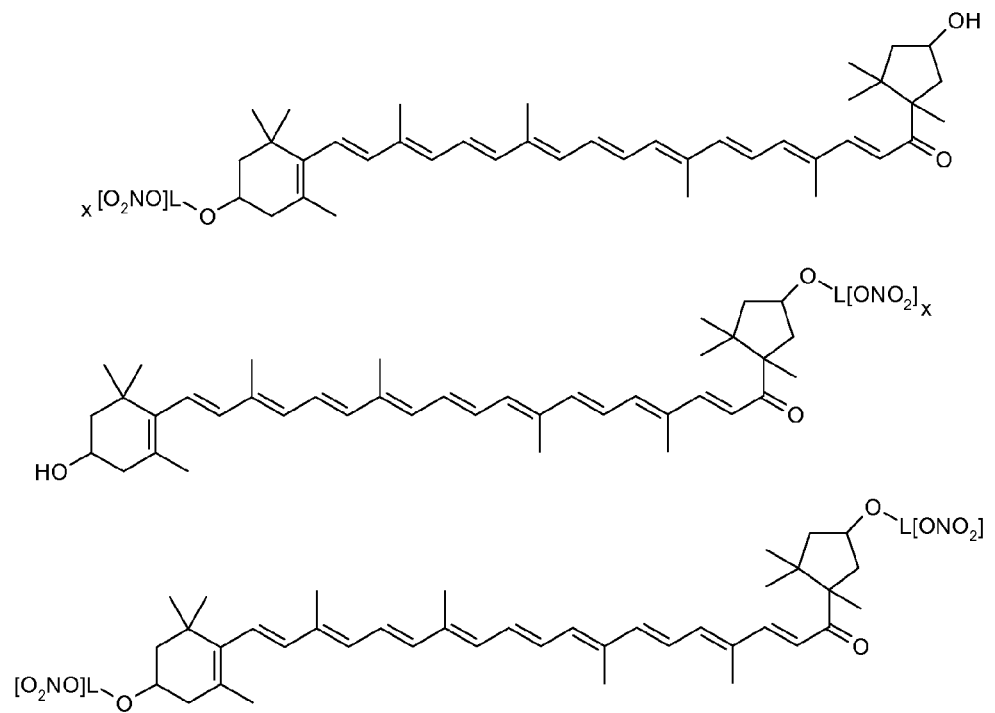
FIG. 5 are structural formulas depicting capsanthin nitrooxy alkanoates and a capsanthin dinitrooxy dialkanoate.
Figure 6:
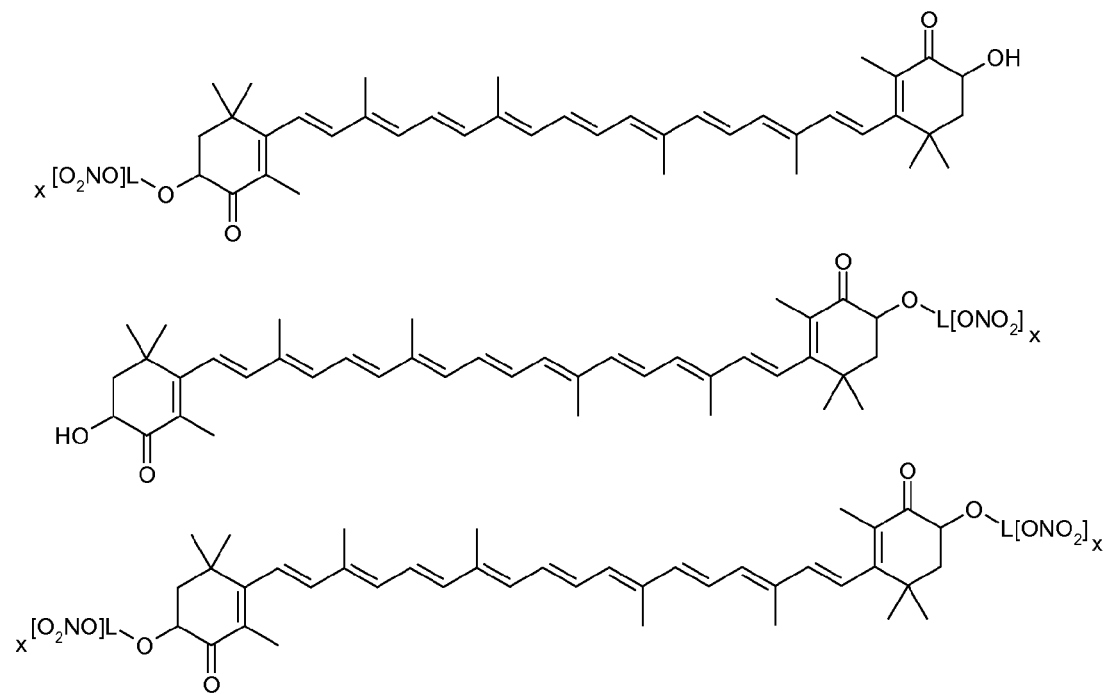
FIG. 6 are structural formulas depicting astaxanthin nitrooxy alkanoates and an astaxanthin dinitrooxy dialkanoate.

Nitrooxyesters of xanthophylls such as cryptoxanthin nitrooxy alkanoate, flavoxanthin nitrooxy alkanoate (2 possibilities), flavoxanthin dinitrooxy dialkanoate, rubixanthin nitrooxy alkanoate (all see FIG. 3), lutein nitrooxy alkanoate (2 possibilities; see FIG. 4), lutein dinitrooxy alkanoate (see FIG. 4), capsanthin nitrooxy alkanoate (2 possibilities; see FIG. 5), capsanthin dinitrooxy dialkanoate (see FIG. 5), astaxanthin nitrooxy alkanoate (2 possibilities, see FIG. 6), astaxanthin dinitrooxy dialkanoate (see FIG. 6), zeaxanthin

IV

Figure 7:
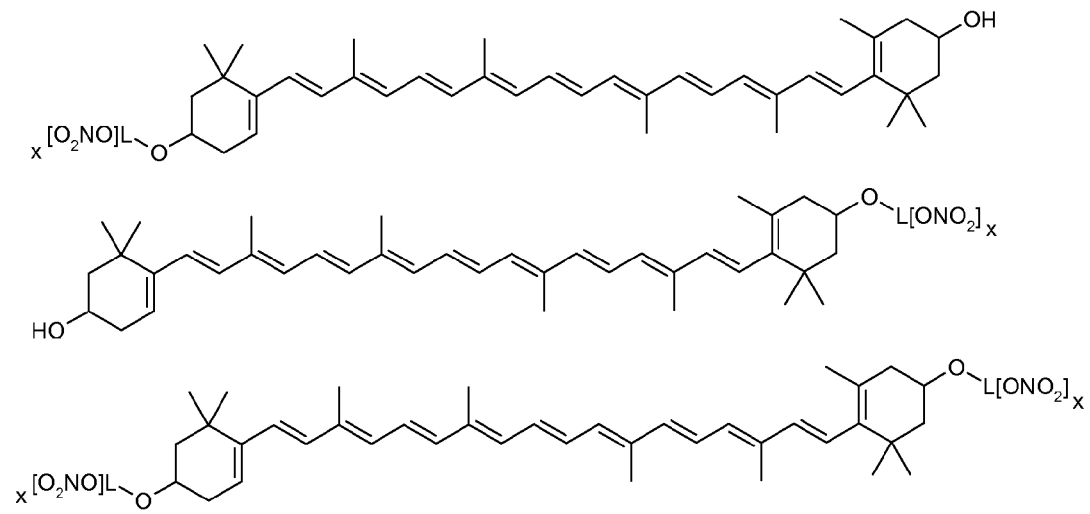
FIG. 7 are structural formulas depicting zeaxanthin nitrooxy alkanoates and a zeaxanthin dinitrooxy dialkanoate.
Figure 10:
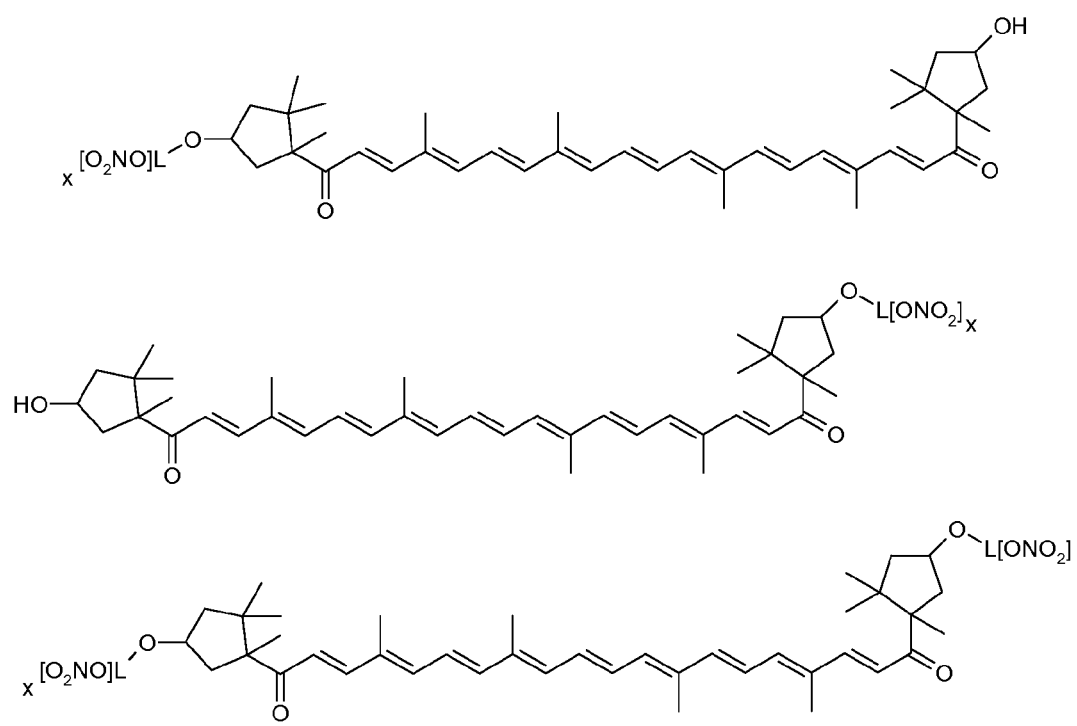
FIG. 10 are structural formulas depicting capsorubin nitrooxy alkanoates and a capsorubin dinitrooxy dialkanoate.
Figure 11:
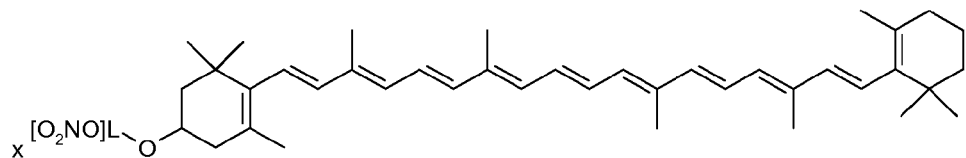
FIG. 11 is a structural formula depicting β-cryptoxanthin nitrooxyester.

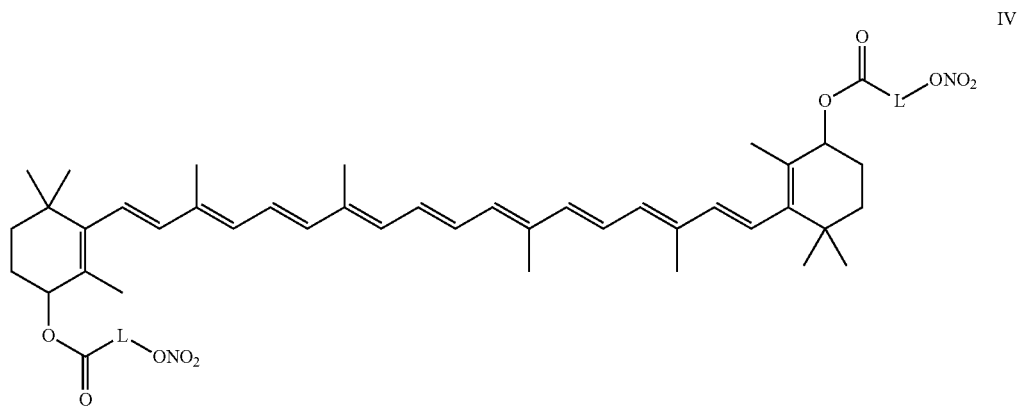

nitrooxy alkanoate (2 possibilities, see FIG. 7), zeaxanthin dinitrooxy dialkanoate (see FIG. 7), isozeaxanthin nitrooxy alkanoate (2 possibilities), isozeaxanthin dinitrooxy dialkanoate (see FIG. 1), as well as capsorubin nitrooxy alkanoate (2 possibilities, see FIG. 10), capsorubin dinitrooxy dialkanoate (see FIG. 10) and β-cryptoxanthin nitrooxyester (see FIG. 11) are not known in the art.

Figure 8:
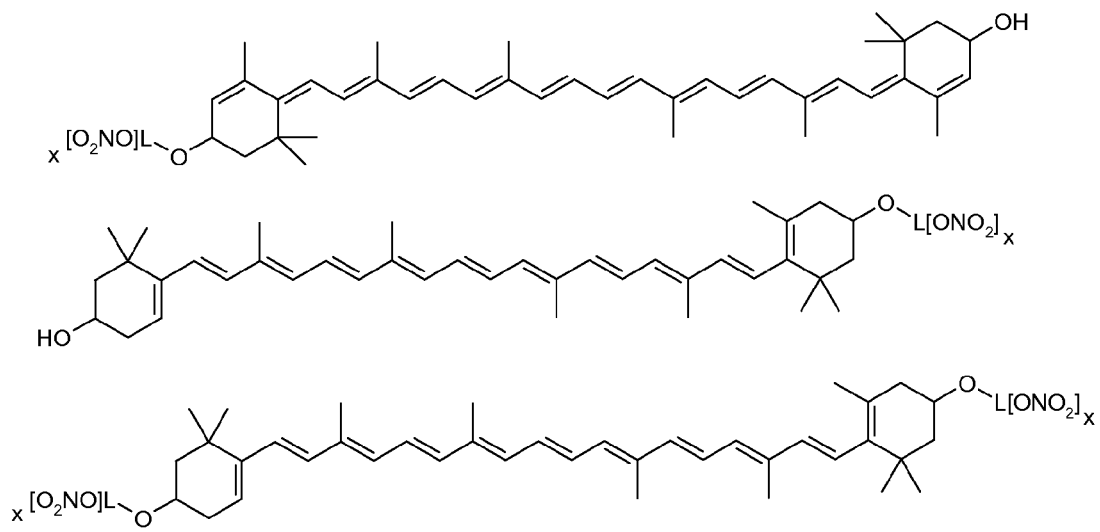
FIG. 8 are structural formulas depicting mono- and dinitrooxyesters of 4',5'-didehydro-retro-b-carotene-3,3'-diol.
Figure 9:
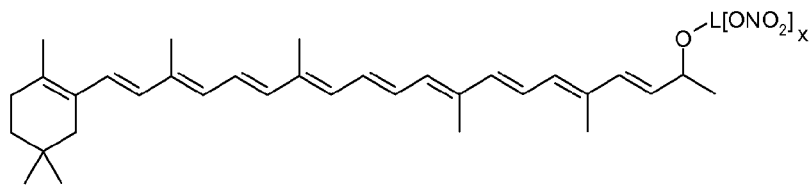
FIG. 9 is a structural formula depicting the nitrooxyester of 5,9,14,18-tetramethyl-20-(2,6,6-trimethyl-1-cyclohexen-1-yl)-3,5,7,9,11,13,15,17,19-eicosanonaen-2-ol.

Further until now unknown compounds of formula I are mono- and dinitrooxyester of 4',5'-didehydro-retro-b-carotene-3,3'-diol (see FIG. 8) [hydrogenated rhodoxanthin], as well as the nitrooxyester of 5,9,14,18-tetramethyl-20-(2,6,6-trimethyl-1-cyclohexen-1-yl)-3,5,7,9,11,13,15,17,19-eicosanonaen-2-ol (especially of all-trans 5,9,14,18-tetramethyl-20-(2,6,6-trimethyl-1-cyclohexen-1-yl)-3,5,7,9,11,13,15,17,19-eicosanonaen-2-ol) (see FIG. 9) [hydrogenated citranaxanthin].

Thus, the present invention is also directed to these novel compounds.

In the examples shown in FIGS. 1 and 3-11 $R^1X^1$— is selected from the following group [$X^1=C_9-C_{20}$]:

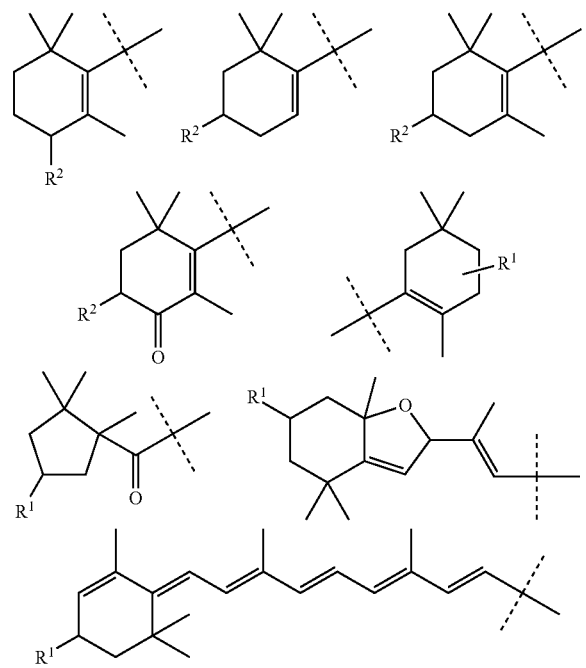

$R^2X^2$— is selected from the following group [$X^2=C_2-C_{10}$]:

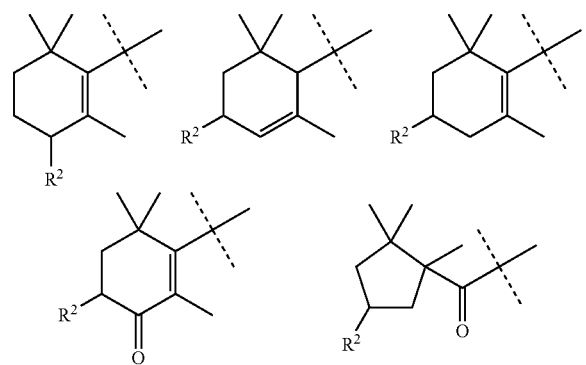

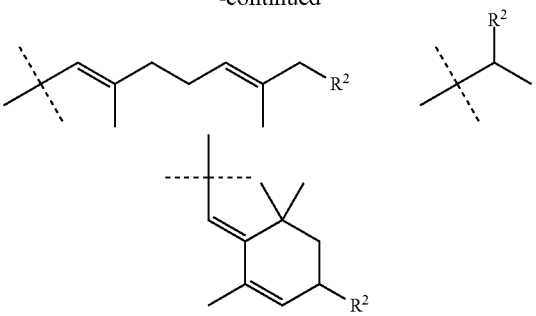

$R^1$ and $R^2$ are independently from each other H, OH or $OL[ONO_2]_x$, with L being a straight alkylene having 2 to 25 carbon atoms, a branched alkylene having 3 to 25 carbon atoms or a cyclic alkylene having 3 to 25 carbon atoms or arylene having 6 to 16 carbon atoms or alkylarylene having 7 to 16 carbon atoms, and x being an integer ≥1 depending on the chain length and with the proviso that at least one of $R^1$ and $R^2$ is $OL[ONO_2]_x$; n=1 or 2, m=0 or 2, p=0 or 1, $R^5=R^6$=methyl, $R^3=R^4$=H.

Compound of the Formula V

Here the same preferences apply as for the compounds of formula I but with the difference that instead of $O(CO)L[ONO_2]_x$ one or more hydroxy group(s) (OH) are present.

Further preferred compounds of formula V are xanthophylls, as well as carotenoids in which at least one hydroxy group has been introduced.

The Acid Component

The acid component is selected from the group consisting of acids of the formula $HO(CO)L[ONO_2]_x$, acid anhydrides of the formula $[O_2NO]_xL(CO)O(CO)L[ONO_2]_x$, acid halides of the formula $X(CO)L[ONO_2]_x$ and any mixtures thereof.

X is Br or Cl.

L is a straight alkylene having 2 to 25 carbon atoms (preferably a straight alkylene having 4 to 25 carbon atoms), a branched alkylene having 3 to 25 carbon atoms (preferably a branched alkylene having 5 to 25 carbon atoms) or a cyclic alkylene having 3 to 25 carbon atoms (preferably a cyclic alkylene having 5 to 25 carbon atoms) or an arylene having 6 to 16 carbon atoms or an alkylarylene having 7 to 16 carbon atoms such as e.g. tolyl, (o-, m-, p-)xylyl, and mesityl.

x is an integer ≥1 depending on the chain length (preferably x=1 or 2, more preferably x=1).

"Depending on the chain length" means that the amount of nitrooxy ester groups is chosen in such a way that the acid component is still possible to be handled without the risk of exploding under the reaction conditions.

Figure 2:
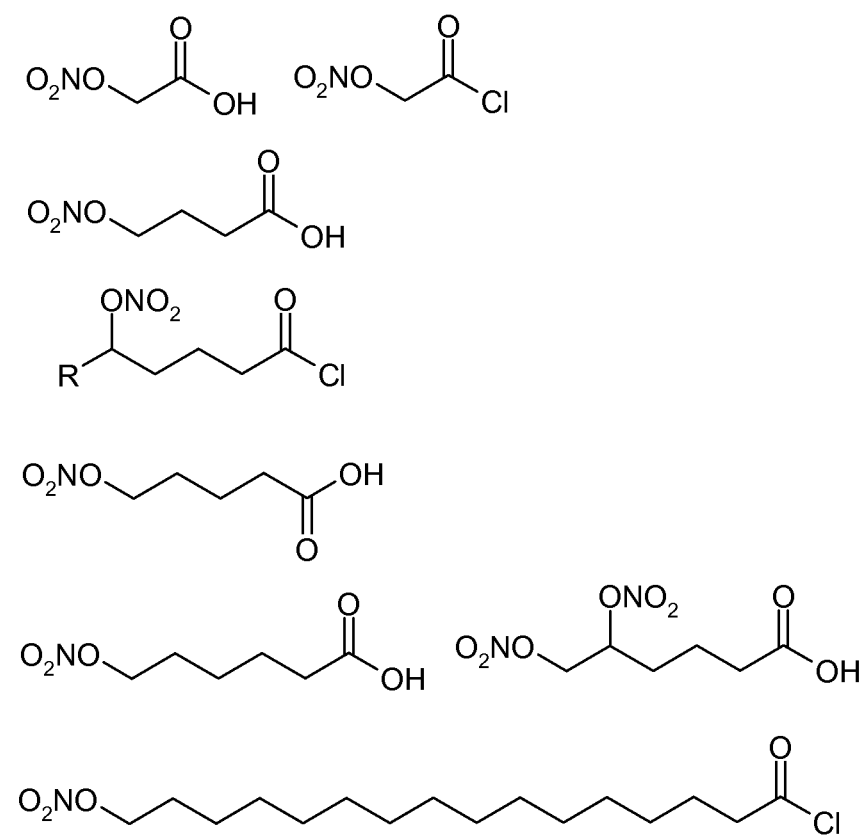
FIG. 2 are structural formulas of the acid component that may be employed in the reaction scheme of FIG. 1.

Examples of acids $HO(CO)L[ONO_2]_x$ and acid chlorides $Cl(CO)L[ONO_2]_x$ are given in FIG. 2.

Substance/Compound b)

The alkyl nitrates may have up to about 25 carbon atoms, preferably from 1 to 12 carbon atoms, more preferably from 2 to 10 carbon atoms. The alkyl group may be either linear or branched or cyclic. That means that cycloalkyl nitrates are also encompassed by the expression "alkyl nitrates". The cycloalkyl nitrates may also be substituted with linear or branched alkyl.

Specific examples of nitrate compounds suitable for use in preferred embodiments include, but are not limited to, the following: methyl nitrate, ethyl nitrate, n-propyl nitrate, isopropyl nitrate, allyl nitrate, n-butyl nitrate, isobutyl nitrate, sec-butyl nitrate, tert-butyl nitrate, n-amyl nitrate, isoamyl nitrate, 2-amyl nitrate, 3-amyl nitrate, tert-amyl nitrate, n-hexyl nitrate, 2-ethylhexyl nitrate, n-heptyl nitrate, sec-heptyl nitrate, n-octyl nitrate, sec-octyl nitrate, n-nonyl nitrate, n-decyl nitrate, n-dodecyl nitrate, cyclopentyl-nitrate, cyclohexylnitrate, methylcyclohexyl nitrate, isopropylcyclohexyl nitrate, and the nitrooxy esters of alkoxy substituted aliphatic alcohols, such as 1-methoxypropyl-2-nitrate, 1-ethoxpropyl-2 nitrate, 1-isopropoxy-butyl nitrate, 1-ethoxylbutyl nitrate and the like.

Preferred alkyl nitrates are ethyl nitrate, propyl nitrate, amyl nitrates, and hexyl nitrates. Other preferred alkyl nitrates are mixtures of primary amyl nitrates or primary hexyl nitrates. By primary is meant that the nitrate functional group is attached to a carbon atom which is attached to two hydrogen atoms. Examples of primary hexyl nitrates include n-hexyl nitrate, 2-ethylhexyl nitrate (2-EHN), 4-methyl-n-pentyl nitrate, and the like. The preparation of the nitrate esters may be accomplished by any of the commonly used methods: such as, for example, esterification of the appropriate alcohol, or reaction of a suitable alkyl halide with silver nitrate.

In many embodiments of the invention 2-ethylhexyl nitrate can make the best contribution to the invention.

It should be understood that pure alkyl nitrates are desired but that mixtures of alkyl nitrates and different purity grade are also suitable. Desirably, many different compositions are made, each having a different alkyl nitrate or more than one alkyl nitrate and/or proportions thereof relative to the compound a), which can be processed under an inert atmosphere, and these compositions are evaluated for their physical properties in different environmental conditions.

Organic peroxides are molecules having an oxygen-oxygen single bond (R—O—O—R'). When the other oxygen bears a hydrogen atom it is called a hydroperoxide (R—O—O—H). In one embodiment of the invention methyl ethyl ketone peroxide is used. A further example is di-t-butyl peroxide.

Compound c)

As in the state of the art (for example U.S. Pat. No. 6,638,324) the fuel may be diesel fuel. It is not important to the invention, if the diesel fuel is selected from biodiesel or from petro-chemical based diesel.

Thus, the term "fuel" encompasses transportation fuels such as low-emission diesel, biodiesel, two-stroke oil, marine bunker fuel, gasoline and jet fuel and stationary-source fuels such as residual fuel oil, low emission diesel and coal.

Petrochemical based diesel fuel, or simply diesel, is a specific fractional distillate of fuel oil (mostly petroleum). The term typically refers to fuel that has been processed from petroleum, but increasingly, alternatives such as biodiesel or biomass to liquid (BTL) or gas to liquid (GTL) diesel that are not derived from petroleum are being developed and adopted.

As described, for example, on the website of the National Biodiesel Board (www.biodiesel.org), biodiesel is a product that may comprise mono-alkyl esters of long chain fatty acids derived from vegetable oils or animal fats. Biodiesel may be produced by acid or base-catalyzed transesterification of the oil with an alcohol. Although methanol is commonly used as the alcohol, other alcohols may also be suitable.

Biodiesel may be blended with petroleum diesel for use in motor vehicles. The blends are commonly described as "BXX", where XX is the percent biodiesel in the blend. B20, for example, is 20% biodiesel, 80% conventional diesel. B100 is 100% biodiesel. The term biodiesel is technically the pure fuel produced by the transesterification process, where the biodiesel is conventional biodiesel. The blends are more properly described as BXX. Although B20 is commonly described as "biodiesel", the term B20 may be preferred to distinguish over pure biodiesel, B100.

A wide spread diesel fuel, which is useful to be included into the mixture, is No. 2 diesel fuel.

The ratio between the composition of the invention (compounds a) and b)) and the fuel, particularly the diesel fuel can vary widely. In certain embodiments of the invention it is advantageous to mix both constituents in a ratio of composition to fuel, particularly to diesel fuel, between 1:10,000,000 and 1:1000.

The diesel fuel may be used for operating any transportation vehicle like cars, buses, motorcycles and ships, i.e. for any two-strike engine or four cycle engine, as well as for any thermic power plant.

In one embodiment of the invention the mixtures can be formulated by the following method. Under an inert atmosphere, (e.g., nitrogen, helium, or argon) the compound a), e.g. isozeaxanthin dinitrooxyester, is dissolved in a solvent (liquid hydrocarbon carrier) such as toluene with heating and stirring. After cooling to ambient temperature compound b) and optionally compound d) are added. The resulting mixture is then added to the fuel.

As shown in the examples, emissions from the oxidation of hydrocarbons such as fuel may be lower when the compounds a) of the invention are mixed to the hydrocarbons than emissions that do not comprise the compounds a) of the present invention.

Compound d)

The compositions according to the present invention may further comprise a stabilizing component. This component may be selected from the group consisting of: 2,2,4-tri-methyl-6-ethoxy-1,2-dihydroquinoline; ethoxyquinoline; 6-ethoxy-2,2,4-trimethyl-1H-quinoline, 2-tert-butylphenol; 2,6-di-tert-butylphenol; 2-tert-butyl-4-n-butylphenol; 2,4,6-tri-tert-butylphenol; 2,6-di-tert-butyl-4-n-butylphenol; 2,6-di-t-butyl-4-methylphenol (=BHT); 2(3)-tert-butyl-4-methoxyphenol (=BHA); 2,2'-methylene-bis(6-t-butyl-4-methylphenol); n-octadecyl 3-(3,5-di-t-butyl-4-hydroxyphenyl)propionate; 1,1,3-tris(3-t-butyl-6-methyl-4-hydroxyphenyl)butane; pentaerythrityltetrakis[3-(3,5-di-t-butyl-4-hydroxyphenyl)propionate]; di-n-octadecyl(3,5-di-t-butyl-4-hydroxybenzyl)phosphonate; 2,4,6-tris(3,5-di-t-butyl-4-hydroxybenzyl)mesitylene; tris(3,5-di-t-butyl-4-hydroxybenzyl)iso-cyanurate; N,N'-diphenylphenylenediamine; p-octyldiphenylamine; p,p-dioctyldiphenyl-amine; N-phenyl-1-naphthylamine; N-phenyl-2-naphthylamine; N-(p-dodecyl)phenyl-2-naphthylamine; di-1-naphthylamine; and di-2naphthylamine; phenothazines; N-alkyl-phenothiazines; imino(bisbenzyl); 6-(t-butyl)phenol; 4-methyl-2,6-di-(t-butyl)phenol; 4,4'-methylenebis(-2,6-di-(t-butyl)phenol); a diphenylamine and a dinaphthylamine.

Compound e)

Many solvents are known to the person of skill. In one embodiment of the invention an aromatic solvent can be used. Examples include benzene, toluene and (m-, p-, o-)xylene and related solvents, as well as mixtures thereof. In one embodiment toluene can be advantageously used.

In another embodiment of the invention the solvent can comprise nonaromatic solvents, such as aliphatic solvents like alkanes and alkanones. Examples include hexane, heptane, octane, nonane, decane, cyclohexane, cyclohexanone and related solvents, as well as mixtures thereof. Cyclohexanone is preferred.

It is also possible to use mixtures of (different) aromatic and non-aromatic solvents like the mixture of toluene and hexane.

Compositions of the Present Invention

In the embodiment of the invention the compound b) is added to compound a) preferably in a solvent. In other embodiments variations in the order of addition can be made.

Moreover compound a) may also be first added to a hydrocarbon followed by compound b) or vice versa. Thus, the present invention is also directed to: a composition comprising
- a compound selected from the group consisting of compounds of the formula I (nitrooxyester), nitrooxyesters of carotenoids, nitrooxyesters of xanthophylls and any mixtures thereof; and
- a hydrocarbon.

Furthermore compound a) may also be first added to a fuel followed by compound b) or vice versa. Thus, the present invention is also directed to:
a composition comprising
- a compound selected from the group consisting of compounds of the formula I (nitrooxyester), nitrooxyesters of carotenoids, nitrooxyesters of xanthophylls and any mixtures thereof; and
- a fuel.

A further embodiment of the present invention is a composition comprising
a) a compound selected from the group consisting of compounds of the formula I (nitrooxyester), nitrooxyesters of carotenoids, nitrooxyesters of xanthophylls and any mixtures thereof; and
b) 2-ethylhexyl nitrate and/or di-t-butyl peroxide; and
d) a stabilizing compound, preferably selected from the group consisting of 6-ethoxy-2,2,4-trimethyl-1H-quinoline, 2,6-di-t-butyl-4-methylphenol (=BHT) and 2(3)-tert-butyl-4-methoxyphenol (=BHA) and mixtures thereof; and
e) toluene.

Another embodiment of the present invention is a composition comprising
a) a compound selected from the group consisting of compounds of the formula I (nitrooxyester), nitrooxyesters of carotenoids, nitrooxyesters of xanthophylls and any mixtures thereof; and
b) 2-ethylhexyl nitrate; and
d) 6-ethoxy-2,2,4-trimethyl-1H-quinoline (EMQ); and
e) optionally toluene.

A further embodiment of the present invention is a composition comprising
a) a compound selected from the group consisting of compounds of the formula I (nitrooxyester), nitrooxyesters of carotenoids, nitrooxyesters of xanthophylls and any mixtures thereof; and
b) 2-ethylhexyl nitrate; and
d) 6-ethoxy-2,2,4-trimethyl-1H-quinoline (EMQ); and
e) toluene.

Also an embodiment of the present invention is a composition comprising
a) a compound selected from the group consisting of compounds of the formula I (nitrooxyester), nitrooxyesters of carotenoids, nitrooxyesters of xanthophylls and any mixtures thereof; and
b) 2-ethylhexyl nitrate.

Preferred are, however, compositions that do not contain 2-ethylhexyl nitrate or any other nitrates or any other organic peroxides or any ignition accelerator, i.e.

◇ compositions comprising
a) a compound selected from the group consisting of compounds of the formula I (nitrooxyester), nitrooxyesters of carotenoids, nitrooxyesters of xanthophylls and any mixtures thereof; and
d) a stabilizing compound, preferably selected from the group consisting of 6-ethoxy-2,2,4-trimethyl-1H-quinoline, 2,6-di-t-butyl-4-methylphenol (=BHT) and 2(3)-tert-butyl-4-methoxyphenol (=BHA) and mixtures thereof; and
e) toluene.

◇ compositions comprising
a) a compound selected from the group consisting of compounds of the formula I (nitrooxyester), nitrooxyesters of carotenoids, nitrooxyesters of xanthophylls and any mixtures thereof; and
d) 6-ethoxy-2,2,4-trimethyl-1H-quinoline (EMQ); and
e) optionally toluene.

◇ compositions comprising
a) a compound selected from the group consisting of compounds of the formula I (nitrooxyester), nitrooxyesters of carotenoids, nitrooxyesters of xanthophylls and any mixtures thereof; and
d) 6-ethoxy-2,2,4-trimethyl-1H-quinoline (EMQ); and
e) toluene.

◇ compositions comprising
a) a compound selected from the group consisting of compounds of the formula I (nitrooxyester), nitrooxyesters of carotenoids, nitrooxyesters of xanthophylls and any mixtures thereof.

Further Components

The composition according to the present invention may further contain one or more of the following components.

Long Chain Fatty Acids and/or Esters

In another embodiment components selected from the group of long chain fatty acids, long chain fatty esters, and any combination thereof can be added to the compositions according to the invention. As used herein, the term "long chain" refers to a molecule with a carbon chain of about 16 carbons atoms or greater, especially of about 16-50 C atoms. The long chain fatty acids or esters may also comprise, for example, meadow foam oil, jojoba oil, or mixtures thereof. Other oils that may comprise long chain fatty acids or esters may also be suitable. Synthetic long chain fatty acids or esters may also be suitable. Other components such as stabilizing compounds, or other components may be added as additional components.

The long chain fatty acids or esters and the solvent are optional components of the composition according to embodiments of the present invention.

Plant Extracts, Fruit Extracts, Herbs Extracts Etc.

In one embodiment of the invention the composition may include a further constituent selected from the group consisting of plant extracts, plant concentrates, herbs extracts, fruit extracts, any and all oil extracts of fruits, vegetables, flowers, grasses, natural grains, leaves from trees, leaves from hedges, hay, any living plant or tree, and combinations or mixtures thereof.

Examples are broccoli concentrate, spinach concentrate, tomato concentrate, kale concentrate, cabbage concentrate, brussels sprouts concentrate, curcumin extract, cranberry and cranberry powder extract, pineapple extract, pineapple leaves extract, rosemary extract, grape seed extract, *ginkgo biloba* extract, ginger root extract, hawthorn berry extract, bilberry extract, oil extract of marigolds, any and all oil extracts of carrots, and combinations or mixtures thereof.

Ignition Accelerators

In a preferred embodiment, other conventional ignition accelerators may be used as a further component of the composition of the invention. Conventional ignition accelerators may include, for example, but not limited to, hydrogen peroxide, benzoyl peroxide, di-tert-butyl peroxide (DTBP), cumene hydroperoxide, di-oleal peroxide, soybean hydroperoxide, and di-ethyl peroxide. Other organic peroxides and hydroperoxides may also be suitable. DTBP is an exemplary ignition accelerator.

In an embodiment, the composition according to embodiments of the present invention may additionally comprise an alkyl nitrate in addition to a conventional ignition accelerator. In an embodiment, the compositions according to embodiments of the present invention may comprise both di-tert-butyl peroxide (DTBP) and 2-ethylhexyl nitrate (2-EHN). The 2-EHN may alternatively be added to the compositions of the invention separately from the other components.

Alternatively, another component may supplement the compound a) (the compound of formula I or the nitrooxyester of any carotenoid/xanthophyll from natural sources) including, but not limited to, β-carotene; α-carotene; or additional carotenoids or food pigments from algae; zeaxanthin; cryptoxanthin; lycopene; lutein; astaxanthin and canthaxanthin; phospholipids, green tea extract, milk thistle extract, quercetin, bromelain, polyphenols, flavonoids, butylated hydroxytoluene (BHT), and combinations or mixtures thereof.

Vegetable carotenoids are particularly preferred, including those containing lycopene, lutein, alpha-carotene, other carotenoids from carrots or algae, betatene, and natural carrot extract. In certain particularly preferred embodiments, a substitute for β-carotene is present in an amount sufficient to yield an equivalent vitamin A activity as for a preferred quantity of β-carotene. However, in other embodiments vitamin A activity may not be a preferred method for determining the quantity of substitute, or the substitute may not have an equivalent vitamin A activity.

The following components may be used in combination with compound a) (the compound of formula I or the nitrooxyester of any carotenoid/xanthophyll from natural sources): butylated hydroxytoluene, lycopene, lutein, all types of carotenoids, oil extract from carrots, beets, hops, grapes, marigolds, fruits, vegetables, palm oil, palm kernel oil, palm tree oil, bell pepper, cottonseed oil, rice bran oil, any plant that is naturally orange, red, purple, or yellow in colour that is growing in nature, or any other material that may be a natural oxygen scavenger but yet remains organic in nature. In certain embodiments, one or more of these components may be substituted in whole or in part for the compound of formula I or the nitrooxyester of any carotenoid/xanthophyll from natural sources.

In one embodiment the invention relates to a method of oxidizing a hydrocarbon, comprising
i) bringing the hydrocarbon in contact with a compound a); and
ii) bringing the hydrocarbon in contact with a compound b); and
iii) oxidizing at least part of the hydrocarbon.

Thus, compound a) and b) may be put together (simultaneously) to the hydrocarbon or separately successively. It may also be possible to first add compound b) and then to add compound a) to the hydrocarbon. Furthermore, the compounds a) and b) may first be mixed and then brought in contact with the hydrocarbon. Preferably no compound b) is added.

When compounds d) and e) are also present, it is also possible to first mix all components and then to add the mixture to the hydrocarbon, as well as to pre-mix some of the components and then to add them successively to the hydrocarbon. The order, in which the single compounds or pre-mixes of them are added is not critical.

Hydrocarbons include all chemical compounds that consists only of the elements carbon (C) and hydrogen (H). Hydrocarbons contain a backbone consisting of carbon atoms, called a carbon skeleton with hydrogen atoms attached to that backbone. Hydrocarbons, which are combustible, are the main components of fossil fuels, which include petroleum, coal, and natural gas. Preferred hydrocarbons in the context of the invention are liquid at room temperature.

One form of oxidation, particularly useful in the context of the present invention, is combustion. Combustion is generally defined as the exothermic reaction of substances with oxygen.

The present invention may not only be directed to the combustion of diesel fuel, but also of natural fuel, petrol, crude oil and residual fuel.

The invention is now described in further detail in the following non-limiting examples.

EXAMPLES

Manufacture of 6-nitrooxy hexanoic acid

6-Nitrooxy hexanoic acid is prepared as described in J. Med. Chem. 2006, 49, 2628-2639 by the reaction of 6-bromo hexanoic acid with silver nitrate in dimethylformamide for 17 hours at 23° C.

Manufacture of 4-nitrooxymethyl benzoic acid

4-Nitrooxymethyl benzoic acid is prepared by the reaction of 4-bromomethyl benzoic acid with silver nitrate in acetonitril.

General Procedure for the Synthesis of Nitrooxy Carbonic Acid Diesters of Dihydroxy Carotenoids

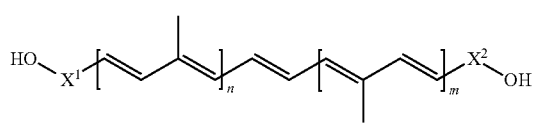

VI

In a 100 ml flask 1.50 mmol of a compound of formula VI (preferably of a carotenoid with 2 hydroxy groups), 4.5 mmol of a nitrooxy carbonic acid (e.g. 6-nitrooxy hexanoic acid) and 0.3 mmol of 4-dimethylaminopyridine are suspended in 21 ml of methylene chloride. To the stirred suspension a solution of 6.0 mmol N,N'-dicyclohexylcarbodiimide in 5 ml methylene chloride is added drop wise over 90 minutes (dosing pump). After stirring overnight at room temperature the reaction mixture is filtered and the filter cake is washed with 10 ml of methylene chloride twice. The filtrate is extracted with 5% aqueous acetic acid (2×25 ml) and water (3×25 ml). The aqueous layer is re-extracted with methylene chloride. The combined organic extracts are dried over sodium sulfate and concentrated under reduced pressure to 10 g. The product is isolated by crystallization from the concentrated solution. The crystals are filtered off, washed and dried in vacuum at 40° C.

Example 1

Isozeaxanthin di-6-nitrooxy hexanoate

For the reaction scheme see FIG. 1.
In a 100 ml flask 0.85 g (1.50 mmol) of isozeaxanthin, 0.84 g (4.5 mmol) of 6-nitrooxy hexanoic acid and 37 mg (0.3 mmol) of 4-dimethylaminopyridine (DMAP) are suspended in 21 ml of methylene chloride. To the stirred suspension a solution of 1.25 g (6.0 mmol) N,N'-dicyclohexylcarbodiimide (DCC) in 5 ml methylene chloride is added drop wise over 90 minutes (dosing pump). After stirring overnight at room temperature the reaction mixture is filtered and the filter cake is washed with 10 ml of methylene chloride twice. The filtrate is extracted with 5% aqueous acetic acid (2×25 ml) and water (3×25 ml). The aqueous layer is re-extracted with methylene chloride. The combined organic extracts are dried over sodium sulfate and concentrated under reduced pressure to 10 g. The product is crystallized by addition of 50 ml of methanol and the red crystals are filtered off, washed with methanol (2×10 ml) and dried in vacuum at 40° C. (61.6% yield).

Example 2

Isozeaxanthin di-6-nitrooxy hexanoate

In a 100 ml flask 0.85 g (1.50 mmol) of isozeaxanthin, 0.70 g (3.75 mmol) of 6-nitrooxy hexanoic acid and 37 mg (0.3 mmol) of 4-dimethylaminopyridine are suspended in 21 ml of methylene chloride. To the stirred suspension a solution of 0.94 g (4.5 mmol) N,N'-dicyclohexylcarbodiimide in 3.8 ml methylene chloride is added drop wise over 45 minutes (dosing pump). After stirring overnight at room temperature another 19 mg (0.15 mmol) of 4-dimethylaminopyridine, 0.35 g (1.88 mmol) of 6-nitrooxy hexanoic acid, 0.47 g of N,N'-dicyclohexylcarbodiimide and 4.8 ml of methylene chloride are added. After 3.5 h the reaction mixture is filtered. Work-up and isolation of the product are carried out according to Example 1 (81.2% yield).

Example 3

Isozeaxanthin di-4-nitrooxy methyl benzoate

Figure 12:
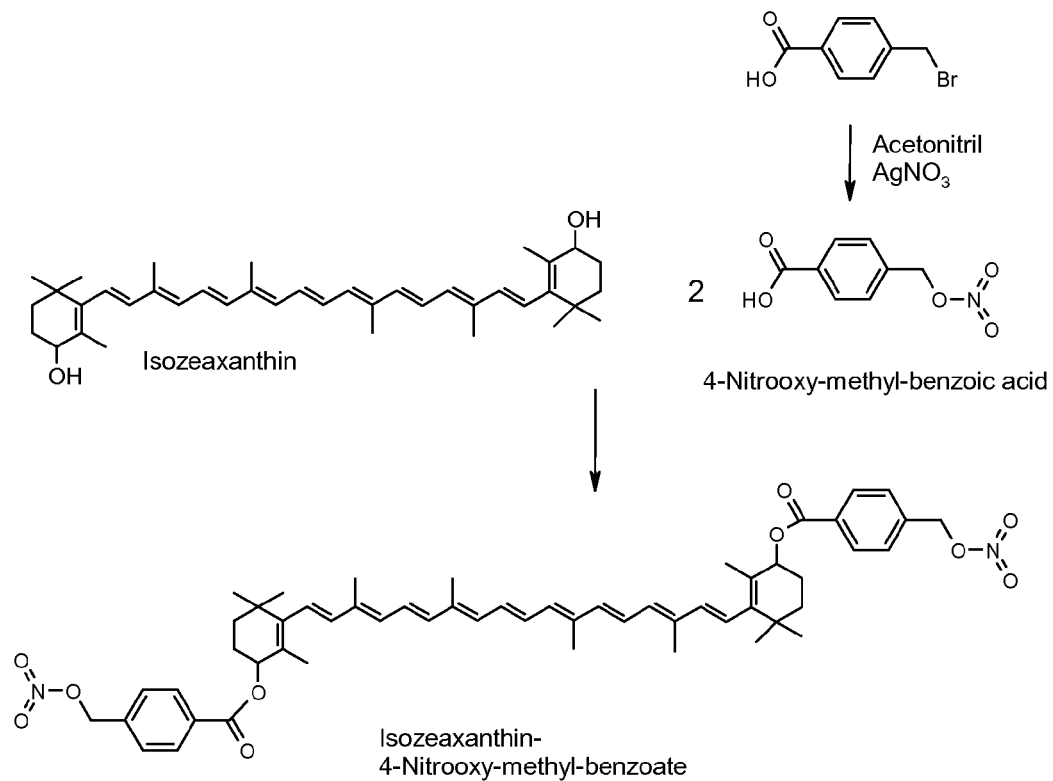
FIG. 12 depicts a reaction scheme to obtain isozeaxanthin di-4-nitrooxy methyl benzoate from isozeaxanthin.

For the reaction scheme see FIG. 12.
In a 100 ml flask 0.85 g (1.50 mmol) of isozeaxanthin, 0.93 g (4.7 mmol) of 4-nitrooxymethyl benzoic acid and 47 mg (0.38 mmol) of 4-dimethylaminopyridine (DMAP) are suspended in 21 ml of methylene chloride. To the stirred suspension a solution of 1.25 g (6.0 mol) N,N'-dicyclohexylcarbodiimide (DCC) in 5 ml methylene chloride is added drop wise over 90 minutes (dosing pump). After stirring overnight at room temperature the reaction mixture is filtered and the filter cake is washed with methylene chloride. The filtrate is concentrated under reduced pressure to 6.2 g. The product is crystallized by addition of 10 ml of hexane. The light-red crystals are filtered off, washed with hexane (2×10 ml) and dried in vacuum at 23° C. Recrystallization from tetrahydrofuran/methanol affords the product in 59% yield.

The invention claimed is:
1. A nitrooxyester of formula I:

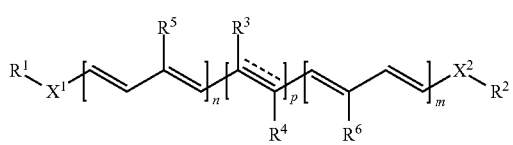

I wherein n, m and p are independently from each other integers from 0 to 50, with the proviso that at least one of n, m and p is not 0 and with the further proviso that n+p+m is at most 50;

$X^1$ and $X^2$ are independently from each other an oxo group or a hydrocarbon moiety which may contain (a) at least one C=C double bond, (b) at least one oxy group and/or (c) at least one oxygen atom;

$R^1$ and $R^2$ are independently from each other hydrogen, hydroxy, alkoxy or $O(CO)[ONO_2]_x$ with L being a straight alkylene having 2 to 25 carbon atoms, a branched alkylene having 3 to 25 carbon atoms, a cyclic alkylene having 3 to 25 carbon atoms, an arylene having 6 to 16 carbon atoms or an alkylarylene having 7 to 16 carbon atoms and with x being an integer 1 depending on chain length;

$R^3$ and $R^4$ are independently from each other hydrogen or in case of a triple bond both do not exist;

$R^5$ and $R^6$ are independently from each other hydrogen or $C_{1-6}$ alkyl; and with the proviso that the compound of formula I contains at least one $O(CO)[ONO_2]_x$ group as defined above.

2. The nitrooxyester according to claim 1, wherein
$X^1$ and $X^2$ are independently from each other a $C_{2-20}$ hydrocarbon moiety, which may contain one or more C=C double bonds, one or more oxy groups and/or one or more oxygen atoms; and/or
wherein $R^1$ and $R^2$ are independently from each other hydrogen, hydroxy, or $O(CO)L[ONO_2]_x$ with L being a straight, branched or cyclic alkylene having 4 to 25 carbon atoms and with x being 1 or 2; and/or
wherein $R^3$ and $R^4$ are independently from each other hydrogen; and/or
wherein $R^5$ and $R^6$ are independently from each other hydrogen or methyl.

3. Nitrooxyesters of carotenoids and nitrooxyesters of xanthophylls, wherein the carotenoids contain at least one hydroxy group.

4. The nitrooxyester of claim 1 which is a xanthophyll nitrooxy ester.

5. The nitrooxyester of claim 1, which is selected from the group consisting of cryptoxanthin nitrooxy alkanoate, flavoxanthin nitrooxy alkanoate, flavoxanthin dinitrooxy dialkanoate, rubixanthin nitrooxy alkanoate, lutein nitrooxy alkanoate, lutein dinitrooxy alkanoate, capsanthin nitrooxy alkanoate, capsanthin dinitrooxy dialkanoate, astaxanthin nitrooxy alkanoate, astaxanthin dinitrooxy dialkanoate, zeaxanthin nitrooxy alkanoate, zeaxanthin dinitrooxy dialkanoate, isozeaxanthin nitrooxy alkanoate, isozeaxanthin dinitrooxy dialkanoate, the mono- and/or dinitrooxyester of 4',5'-didehydro-retro-b-carotene-3,3'-diol, nitrooxyester of 5,9,14,18-tetramethyl-20-(2,6,6-trimethyl-1-cyclohexen-1-yl)-3,5,7,9,11,13,15,17,19-eicosanonaen-2-ol, the mono- and/or dinitrooxyester of capsorubin and β-cryptoxanthin nitrooxyester.

6. The nitrooxyester of claim 4, which is selected from the group consisting of isozeaxanthin nitrooxy alkanoic acid ester, zeaxanthin nitrooxy alkanoic acid ester, astaxanthin nitrooxy alkanoic acid ester, lutein nitrooxy alkanoic acid ester, isozeaxanthin di(nitrooxy alkanoic acid ester), zeaxanthin di(nitrooxy alkanoic acid ester), astaxanthin di(nitrooxy alkanoic acid ester), lutein di(nitrooxy alkanoic acid ester) and mixtures thereof.

7. A composition comprising:
a) a compound selected from the group consisting of nitrooxyesters of formula I as in claim 1, nitrooxyesters of carotenoids, nitrooxyesters of xanthophylls and any mixtures thereof; and
c) a hydrocarbon.

8. The composition according to claim 7, further comprising a compound b) selected from the group consisting of alkyl nitrates, nitrooxy esters of alkoxy substituted aliphatic alcohols and organic peroxides.

9. A composition comprising
a) a compound selected from the group consisting of nitrooxyesters of formula I as in claim 1, nitrooxyesters of carotenoids, nitrooxyesters of xanthophylls and any mixtures thereof; and
b) a substance selected from the group of alkyl nitrates, nitrooxy esters of alkoxy substituted aliphatic alcohols and organic peroxides.

10. The composition of claim 8 wherein compound b) is an alkyl nitrate, especially 2-ethylhexyl nitrate.

11. The composition of claim 7 further comprising a solvent.

12. A composition comprising
a) a compound selected from the group consisting of nitrooxyesters of formula I as in claim 1, nitrooxyesters of carotenoids, nitrooxyesters of xanthophylls and any mixtures thereof;
b) a compound selected from the group consisting of alkyl nitrates, nitrooxy esters of alkoxy substituted aliphatic alcohols, organic peroxides and mixtures thereof;
d) a stabilizing compound; and
e) optionally a solvent.

13. The composition of claim 11, wherein a solvent is present and the solvent comprises an aromatic solvent and/or an aliphatic solvent, preferably hexane, heptane, octane, nonane decane, cyclohexane, benzene, toluene and/or xylene.

14. The composition of claim 7, further comprising a compound selected from the group consisting of long chain fatty acids, long chain fatty esters, and any combination thereof.

15. The composition of claim 7, wherein the compound a) is stabilized with tocopherol and/or tocopherol acetate.

16. The composition of claim 12, wherein the stabilizing compound is selected from the group consisting of: 2,2,4-trimethyl-6-ethoxy-1,2-di-hydroquinoline; ethoxyquinoline; 6-ethoxy-2,2,4-trimethyl-1H-quinoline 2-tert-butylphenol; 2,6-di-tert-butylphenol; 2-tert-butyl-4-n-butylphenol; 2,4,6-tri-tert-butylphenol; 2,6-di-tert-butyl-4-n-butylphenol; 2,6-di-t-butyl-4-methylphenol; 2(3)-tert-butyl-4-methoxyphenol; 2,2'-methylene-bis(6-t-butyl-4-methylphenol); n-octadecyl 3-(3,5-di-t-butyl-4-hydroxyphenyl) propionate; 1,1,3-tris(3-t-butyl-6-methyl-4-hydroxyphenyl) butane; pentaerythrityltetrakis[3-(3,5-di-t-butyl-4-hydroxyphenyl)propionate]; di-n-octadecyl(3,5-di-t-butyl-4-hydroxybenzyl) phosphonate; 2,4,6-tris(3,5-di-t-butyl-4-hydroxybenzyl) mesitylene; tris(3,5-di-t-butyl-4-hydroxybenzyl)isocyanurate; N,N'-diphenylphenylenediamine; p-octyldiphenylamine; p,p-dioctyldiphenylamine; N-phenyl-1-naphthylamine; N-phenyl-2-naphthylamine; N-(p-dodecyl)phenyl-2-naphthylamine; di-1-naphthylamine; and di-2naphthylamine; phenothazines; N-alkylphenothiazines; imino(bisbenzyl); 6-(t-butyl)phenol; 4-methyl-2,6-di-(t-butyl) phenol; 4,4'-methylenebis(-2,6-di-(t-butyl)phenol); a diphenylamine and a dinaphthylamine.

17. The composition of claim 9 further comprising a hydrocarbon molecule.

18. The composition according to claim 7, wherein the compound a) is selected from the group consisting of iso-zeaxanthin nitrooxyesters and their mixtures, iso-zeaxanthin dinitrooxyesters and their mixtures, mixtures of iso-zeaxantin with iso-zeaxanthin nitrooxyesters, mixtures of iso-zeaxantin with iso-zeaxanthin dinitrooxyesters, and mixtures of iso-zeaxantin with iso-zeaxanthin nitrooxyesters and iso-zeaxanthin dinitrooxyesters.

19. A composition comprising:
a) a compound selected from the group consisting of nitrooxyesters of formula I as in claim 1, nitrooxyesters of carotenoids, nitrooxyesters of xanthophylls and any mixtures thereof;
b) 2-ethylhexyl nitrate and/or di-t-butyl peroxide;
d) a stabilizing compound, preferably selected from the group consisting of 6-ethoxy-2,2,4-trimethyl-1H-quinoline, 2,6-di-t-butyl-4-methylphenol and 2(3)-tert-butyl-4-methoxyphenol and mixtures thereof; and
e) optionally toluene.

20. A method of oxidizing a hydrocarbon, comprising
i) bringing the hydrocarbon in contact with a nitrooxyester according to claim 1; and
ii) bringing the hydrocarbon in contact with compound b) selected from the group consisting of alkyl nitrates, nitrooxy esters of alkoxy substituted aliphatic alcohols, organic peroxides and mixtures thereof; and
iii) oxidizing at least part of the hydrocarbon.

21. A mixture comprising a composition according to claim 9 and a fuel.

22. The mixture of claim 21, wherein the fuel is a diesel fuel.

23. The mixture of claim 22, wherein the diesel fuel is selected from the group consisting of biodiesel and petrochemical based diesel.

24. The mixture of claim 22 wherein a ratio of the composition to the diesel fuel is between 1:10,000,000 and 1:1000.

25. The mixture of claim 22 wherein the diesel fuel comprises No. 2 diesel fuel.

26. A composition comprising
a) a compound selected from the group consisting of iso-zeaxanthin nitrooxyesters and their mixtures, iso-zeaxanthin dinitrooxyesters and their mixtures, mixtures of iso-zeaxantin with iso-zeaxanthin nitrooxyesters, mixtures of iso-zeaxantin with iso-zeaxanthin dinitrooxyesters, and mixtures of iso-zeaxantin with iso-zeaxanthin nitrooxyesters and iso-zeaxanthin dinitrooxyesters; and
b) 2-ethylhexyl nitrate; and
d) 6-ethoxy-2,2,4-trimethyl-1H-quinoline; and
e) optionally toluene.

27. A composition comprising:
a) a compound selected from the group consisting of iso-zeaxanthin nitrooxyesters and their mixtures, iso-zeaxanthin dinitrooxyesters and their mixtures, mixtures of iso-zeaxantin with iso-zeaxanthin nitrooxyesters, mixtures of iso-zeaxantin with iso-zeaxanthin dinitrooxyesters, and mixtures of iso-zeaxantin with iso-zeaxanthin nitrooxyesters and iso-zeaxanthin dinitrooxyesters; and
b) 2-ethylhexyl nitrate.

28. A process for the manufacture of compounds of formula I

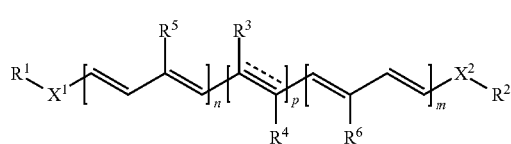

comprising the step of reacting a compound of formula V

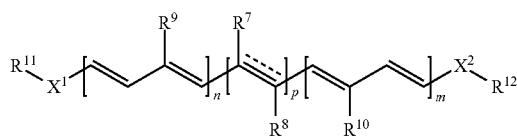

with an acid of the formula $HO(CO)L[ONO_2]_x$ or an acid anhydride of the formula $[O_2NO]_xL(CO)O(CO)L[NO_2]_x$ or an acid halide of the formula $X(CO)L[ONO_2]_x$ with X being Br or Cl and L being a straight alkylene having 2 to 25 carbon atoms, a branched or cyclic alkylene having 3 to 25 carbon atoms, an arylene having 6 to 16 carbon atoms or an alkylarylene having 7 to 16 carbon atoms and with x being an integer ≥1 depending on the chain length (preferably x=1 or 2, more preferably x=1);

wherein n, m and p are independently from each other integers from 0 to 50, with the proviso that at least one of n, m and p is not 0 and with the further proviso that n+p+m is at most 50;

$X^1$ and $X^2$ are independently from each other an oxo group or a straight, branched or cyclic alkylene group, which may contain (a) C=C double bond(s) and/or (an) oxy group(s) and/or (an) oxygen atom(s);

$R^1$ and $R^2$ are independently from each other hydrogen, hydroxy, alkoxy or $O(CO)L[ONO_2]_x$ with L and x as defined above;

$R^3$ and $R^4$ are independently from each other hydrogen or in case of a triple bond both do not exist;

$R^5$ and $R^6$ are independently from each other hydrogen or $C_{1-6}$ alkyl;

$R^{11}$ and $R^{12}$ are independently from each other hydrogen, hydroxy or alkoxy;

$R^7$ and $R^8$ are independently from each other hydrogen or in case of a triple bond both do not exist;

$R^9$ and $R^{10}$ are independently from each other hydrogen or $C_{1-6}$ alkyl;

with the proviso that the compound of formula V itself contains at least one hydroxy group and the further proviso that the compound of formula I itself contains at least one $O(CO)L[ONO_2]_x$ group as defined above.

29. The composition of claim 7, wherein the hydrocarbon is a hydrocarbon fuel.

30. The composition of claim 15, wherein the compound a) is stabilized with less than 10% by weight of tocopherol and/or tocopherol acetate based on the weight of compound a).

31. The composition of claim 15, wherein the compound a) is stabilized with less than 0.1 to 5% by weight of tocopherol and/or tocopherol acetate based on the weight of compound a).

32. The composition of claim 15, wherein the compound a) is stabilized with less than 0.5 to 3 wt. % by weight of tocopherol and/or tocopherol acetate based on the weight of compound a).

* * * * *